US012569424B2

(12) United States Patent
Thomas

(10) Patent No.: US 12,569,424 B2
(45) **Date of Patent: *Mar. 10, 2026**

(54) STABLE VITAMIN C COMPOSITIONS

(71) Applicant: MARY KAY INC., Addison, TX (US)

(72) Inventor: Isaac Thomas, Carrollton, TX (US)

(73) Assignee: MARY KAY INC., Addison, TX (US)

( * ) Notice: Subject to any disclaimer, the term of this patent is extended or adjusted under 35 U.S.C. 154(b) by 299 days.

This patent is subject to a terminal disclaimer.

(21) Appl. No.: 18/234,592

(22) Filed: Aug. 16, 2023

(65) Prior Publication Data

US 2023/0390177 A1 Dec. 7, 2023

Related U.S. Application Data

(63) Continuation of application No. 17/143,757, filed on Jan. 7, 2021, now Pat. No. 11,771,638, which is a continuation of application No. 15/954,364, filed on Apr. 16, 2018, now Pat. No. 10,912,729, which is a continuation of application No. 14/328,972, filed on Jul. 11, 2014, now Pat. No. 9,968,539, which is a continuation of application No. 11/677,266, filed on Feb. 21, 2007, now Pat. No. 8,865,228.

(60) Provisional application No. 60/775,734, filed on Feb. 21, 2006.

(51) Int. Cl.

| | |
|---|---|
| ***A61K 8/67*** | (2006.01) |
| ***A61K 8/02*** | (2006.01) |
| ***A61K 8/58*** | (2006.01) |
| ***A61K 8/92*** | (2006.01) |
| ***A61K 8/9706*** | (2017.01) |
| ***A61K 8/9761*** | (2017.01) |
| ***A61K 8/9767*** | (2017.01) |
| ***A61K 8/9789*** | (2017.01) |
| ***A61K 8/9794*** | (2017.01) |
| ***A61K 31/375*** | (2006.01) |
| ***A61K 47/24*** | (2006.01) |
| ***A61K 47/44*** | (2017.01) |
| ***A61Q 17/04*** | (2006.01) |
| ***A61Q 19/08*** | (2006.01) |

(52) U.S. Cl.

CPC ................ *A61K 8/676* (2013.01); *A61K 8/02* (2013.01); *A61K 8/0245* (2013.01); *A61K 8/585* (2013.01); *A61K 8/922* (2013.01); *A61K 8/9706* (2017.08); *A61K 8/9761* (2017.08); *A61K 8/9767* (2017.08); *A61K 8/9789* (2017.08); *A61K 8/9794* (2017.08); *A61K 31/375* (2013.01); *A61K 47/24* (2013.01); *A61K 47/44* (2013.01); *A61Q 17/04* (2013.01); *A61Q 19/08* (2013.01); *A61K 2800/31* (2013.01); *A61K 2800/412* (2013.01); *A61K 2800/52* (2013.01)

(58) Field of Classification Search
None
See application file for complete search history.

(56) References Cited

U.S. PATENT DOCUMENTS

| | | | |
|---|---|---|---|
| 2,400,171 | A | 5/1946 | Ruskin |
| 2,798,053 | A | 7/1957 | Brown |
| 4,509,949 | A | 4/1985 | Huang et al. |
| 4,564,686 | A | 1/1986 | Ogata |
| 4,599,379 | A | 7/1986 | Flesher et al. |
| 4,628,078 | A | 12/1986 | Glover et al. |
| 4,835,206 | A | 5/1989 | Farrar et al. |
| 4,849,484 | A | 7/1989 | Heard |
| 4,914,197 | A | 4/1990 | Yamamoto et al. |
| 5,087,445 | A | 2/1992 | Haffey et al. |
| 5,100,660 | A | 3/1992 | Hawe et al. |
| 5,306,713 | A | 4/1994 | Suetsugu et al. |
| 5,314,686 | A | 5/1994 | Todd, Jr. |
| 5,415,861 | A | 5/1995 | Duffy et al. |
| 5,472,699 | A | 12/1995 | Duffy et al. |
| 5,560,917 | A | 10/1996 | Cohen et al. |
| 5,583,136 | A | 12/1996 | Yusuf et al. |
| 5,607,968 | A | 3/1997 | Ptchelintsev |
| 5,674,511 | A | 10/1997 | Kacher et al. |
| 5,705,144 | A | 1/1998 | Harding et al. |
| 5,736,567 | A | 4/1998 | Cantin et al. |
| 5,738,859 | A | 4/1998 | Posner |
| 5,750,123 | A | 5/1998 | Znaiden et al. |
| 5,776,438 | A | 7/1998 | Tokue et al. |
| 5,853,741 | A | 12/1998 | Znaiden et al. |
| 5,879,692 | A | 3/1999 | Hamano et al. |
| 5,885,948 | A | 3/1999 | Glenn, Jr. et al. |
| 5,888,984 | A | 3/1999 | Brown |

(Continued)

FOREIGN PATENT DOCUMENTS

| | | |
|---|---|---|
| EP | 1 082 082 | 12/2003 |
| JP | 4-149113 | 5/1992 |

(Continued)

OTHER PUBLICATIONS

"What is a Moisturizer and How to Choose One." *Preserv Skincare*, Dec. 19, 2020, https://www.preservskincare.com/blog/what-is-a-moisturizer-and-how-to-choose-one. Accessed Mar. 24, 2023.
Budowski, "Sesame Oil. III. Antioxidant Properties of Sesmol," *The Journal of the American Oil Chemists' Society*, 1950, 264-267.
Fitzpatrick et al., "Double-blind, half-face study comparing topical vitamin C and vehicle for rejuvenation of photodamage," *Dermatol. Surg.*, 28(3):231-236, 2002.
Humbert, "Topical vitamin C in the treatment of photoaged skin," *Eur. J. Dermatol.*, 11:172-173, 2001.

(Continued)

*Primary Examiner* — Anand U Desai
*Assistant Examiner* — Catheryne Chen
(74) *Attorney, Agent, or Firm* — NORTON ROSE FULBRIGHT US LLP

(57) ABSTRACT

A composition including ascorbic acid, a silicone oil, and at least 15% by weight of an essential oil is disclosed. At least 50% of the initial amount of ascorbic acid in the non-aqueous composition can remain stable when the composition is stored for at least 1 month at room temperature.

20 Claims, No Drawings

(56) References Cited

U.S. PATENT DOCUMENTS

| | | | |
|---|---|---|---|
| 5,902,591 | A | 5/1999 | Herstein |
| 5,922,335 | A | 7/1999 | Ptchelintsev |
| 5,935,559 | A | 8/1999 | Afriat et al. |
| 5,952,001 | A | 9/1999 | Meybeck et al. |
| 5,997,890 | A | 12/1999 | Sine et al. |
| 6,004,567 | A | 12/1999 | Marchi-Lemann et al. |
| 6,015,548 | A | 1/2000 | Siddiqui et al. |
| 6,036,946 | A | 3/2000 | Greene |
| 6,080,707 | A | 6/2000 | Glenn, Jr. et al. |
| 6,080,708 | A | 6/2000 | Glenn, Jr. et al. |
| 6,103,267 | A | 8/2000 | Mitchnick et al. |
| 6,110,476 | A | 8/2000 | Nguyen et al. |
| 6,132,737 | A | 10/2000 | Wolf et al. |
| 6,132,745 | A | 10/2000 | Marchi-Lemann et al. |
| 6,146,664 | A | 11/2000 | Siddiqui |
| 6,153,208 | A | 11/2000 | McAtee et al. |
| 6,174,519 | B1 | 1/2001 | Greene |
| 6,183,766 | B1 | 2/2001 | Sine et al. |
| 6,190,678 | B1 | 2/2001 | Hasenoehrl et al. |
| 6,194,452 | B1 | 2/2001 | Murad |
| 6,235,272 | B1 | 5/2001 | Greene |
| 6,239,174 | B1 | 5/2001 | Afriat et al. |
| 6,328,983 | B1 | 12/2001 | Afriat |
| 6,338,840 | B1 | 1/2002 | Allan et al. |
| 6,346,254 | B1 | 2/2002 | Streicher et al. |
| 6,361,783 | B2 | 3/2002 | Moaddel et al. |
| 6,387,882 | B1 | 5/2002 | Ogata et al. |
| 6,423,329 | B1 | 7/2002 | Sine et al. |
| 6,440,433 | B1 | 8/2002 | Breton et al. |
| 6,465,510 | B2 | 10/2002 | Afriat et al. |
| 6,472,699 | B1 | 10/2002 | Sugiyama et al. |
| 6,475,500 | B2 | 11/2002 | Vatter et al. |
| 6,485,732 | B1 | 11/2002 | Bekele |
| 6,488,947 | B1 | 12/2002 | Bekele |
| 6,491,934 | B1 | 12/2002 | Bekele |
| 6,491,935 | B1 | 12/2002 | Bekele |
| 6,495,150 | B2 | 12/2002 | Bekele |
| 6,524,598 | B2 | 2/2003 | Sunkel et al. |
| 6,541,017 | B1 | 4/2003 | Lemann et al. |
| 6,544,532 | B1 | 4/2003 | Jager-Lezer et al. |
| 6,565,865 | B2 | 5/2003 | Bekele |
| 6,573,299 | B1 | 6/2003 | Petrus |
| 6,576,248 | B1 | 6/2003 | Simard et al. |
| 6,589,514 | B2 | 7/2003 | Jensen et al. |
| 6,589,542 | B2 | 7/2003 | Bekele |
| 6,607,737 | B2 | 8/2003 | Bekele et al. |
| 6,613,341 | B2 | 9/2003 | Motley et al. |
| 6,645,512 | B2 | 11/2003 | Bekele |
| 6,696,049 | B2 | 2/2004 | Vatter et al. |
| 6,703,005 | B2 | 3/2004 | Allan et al. |
| 6,713,075 | B2 | 3/2004 | Bekele |
| 6,716,441 | B1 | 4/2004 | Osborne et al. |
| 6,753,000 | B2 | 6/2004 | Breton et al. |
| 6,793,929 | B2 | 9/2004 | Bleckmann et al. |
| 6,821,934 | B1 | 11/2004 | Bleckmann et al. |
| 6,828,348 | B2 | 12/2004 | Ogata et al. |
| 6,846,846 | B2 | 1/2005 | Modak et al. |
| 6,858,216 | B2 | 2/2005 | Schulze zur Wiesche et al. |
| 6,858,227 | B1 | 2/2005 | Lal et al. |
| 6,864,284 | B2 | 3/2005 | Roomi et al. |
| 6,958,148 | B1 | 10/2005 | Green et al. |
| 2001/0007653 | A1 | 7/2001 | Moaddel et al. |
| 2002/0018760 | A1 | 2/2002 | Vatter et al. |
| 2002/0018790 | A1 | 2/2002 | Vatter et al. |
| 2002/0018791 | A1 | 2/2002 | Vatter et al. |
| 2002/0086039 | A1 | 7/2002 | Lee et al. |
| 2003/0045573 | A1 | 3/2003 | Afriat et al. |
| 2003/0064494 | A1 | 4/2003 | Kumar et al. |
| 2003/0125572 | A1 | 7/2003 | Ogata et al. |
| 2003/0171479 | A1 | 9/2003 | Lennon |
| 2003/0180333 | A1 | 9/2003 | Moaddel et al. |
| 2003/0190336 | A1 | 10/2003 | Adams et al. |
| 2004/0067213 | A1 | 4/2004 | Schmid et al. |
| 2004/0071744 | A1 | 4/2004 | Breton et al. |
| 2004/0071745 | A1 | 4/2004 | Breton et al. |
| 2004/0092482 | A1 | 5/2004 | Gupta |
| 2004/0096406 | A1 | 5/2004 | De Poilly |
| 2004/0105873 | A1 | 6/2004 | Gupta |
| 2004/0121058 | A1 | 6/2004 | Jayalekshmy et al. |
| 2004/0161435 | A1 | 8/2004 | Gupta |
| 2004/0219124 | A1 | 11/2004 | Gupta |
| 2004/0241124 | A1 | 12/2004 | Lannibois-Drean et al. |
| 2005/0074474 | A1 | 4/2005 | Sako |
| 2005/0100570 | A1 | 5/2005 | Wei et al. |
| 2005/0154054 | A1 | 7/2005 | Zielinski et al. |
| 2005/0208003 | A1 | 9/2005 | Gupta |
| 2005/0239670 | A1 | 10/2005 | Stella et al. |

FOREIGN PATENT DOCUMENTS

| | | |
|---|---|---|
| JP | 4-149117 | 5/1992 |
| WO | WO 99/24011 | 5/1999 |
| WO | WO 00/02535 | 1/2000 |
| WO | WO 01/09000 | 2/2001 |

OTHER PUBLICATIONS

International Cosmetic Ingredient Dictionary, 10th edition, 2004.

International Preliminary Report on Patentability, issued in Application No. PCT/US2007/062489, dated Sep. 4, 2008.

Lin et al., "UV photoprotection by combination topical antioxidants vitamin C and vitamin E," *J. Am. Acad. Dermatol.*, 48:866-874, 2003.

Office Communication, issued in Chinese Patent Application No. 200780014399.7, dated Nov. 10, 2010. (English Translation).

Pinnell, "Cutaneous photodamage, oxidative stress, and topical antioxidant protection," *J. Am. Acad. Dermatol.*, 48:1-19; 1-22, 2003.

STABLE VITAMIN C COMPOSITIONS

CROSS-REFERENCE TO RELATED APPLICATIONS

This application is a continuation of U.S. patent application Ser. No. 17/143,757 filed Jan. 7, 2021, which is a continuation of U.S. patent application Ser. No. 15/954,364, filed Apr. 16, 2018, now U.S. Pat. No. 10,912,729, which is a continuation of U.S. patent application Ser. No. 14/328,972, filed Jul. 11, 2014, now U.S. Pat. No. 9,968,536, which is a continuation of U.S. patent application Ser. No. 11/677,266, filed Feb. 21, 2007, now U.S. Pat. No. 8,865,228, which claims the benefit of U.S. Provisional Application No. 60/775,734, filed Feb. 21, 2006. The contents of the referenced applications are incorporated into the present application by reference.

BACKGROUND OF THE INVENTION

A. Field of the Invention

The present invention relates generally to compositions and methods that can be used to stabilize vitamin C.

B. Description of Related Art

Vitamin C is an antioxidant that can benefit the skin when applied topically. Topical use of vitamin C may supplement sunscreen protection and provide additional anticarcinogenic protection. (Pinnel, 2003; Humbert 2001). Topical application of vitamin C can provide additional protection against sun damage (Lin et al., 2003). Vitamin C has been shown to result in clinically visible and statistically significant improvement in wrinkling in humans (Fitzpatrick et al., 2002).

Although topical vitamin C application can benefit the appearance and health of skin, problems limit the use of vitamin C in cosmetic compositions. In particular, vitamin C can be difficult to stabilize in topical compositions. For example, U.S. Pat. No. 2,400,171 discloses the conversion of ascorbic acid to its calcium or zinc salt to maintain stable aqueous solutions. U.S. Pat. No. 6,146,664 explains that the difficulties in preparing a stable vitamin C composition is because the ascorbic acid is an α-ketolactone having a double bond between the second and third carbon atoms of the structure. This combined with the hydroxyl groups at the second and third carbon atoms of vitamin C make vitamin C a fairly strong reducing agent. In aqueous media, therefore, vitamin C looses its beneficial effects because of degradation or reaction with other compounds.

SUMMARY OF THE INVENTION

One aspect of the present invention concerns a composition comprising ascorbic acid or a derivative thereof, a silicone containing compound, and/or an essential oil. The composition can be non-aqueous. The ascorbic acid can be particulate ascorbic acid. The ascorbic acid can be suspended and/or substantially insoluble within the composition. The particulate ascorbic acid can include a particle size of less than about 50 μm. In other aspects, the particle size can be 1, 2, 3, 4, 5, 6, 7, 8, 9, 10, 11, 12, 13, 14, 15, 16, 17, 18, 19, 20, 25, 30, 40, 45, 50, 60, 70, 80, 90, 100, 150, 200, 250, 300, 350, 400, 450, 500, 550, 600, 650, 700, 750, 800, 850, 900, 950, 1000, 2000, 3000, 4000, 5000 μm or larger or any number derivable therein. In certain embodiments, the particulate ascorbic acid is ultra fine powder (e.g., vitamin C particles having a particle size of approximately 75 to 850 μm). In certain non-limiting aspects, the composition can include at least about 5% to about 15%, or from about 7% to about 10%, by weight of the total compositions of the ascorbic acid. However, as noted in other parts of this specification, the amount of vitamin C in the composition can extend beyond these stated ranges. The inventor also contemplates that the compositions of the present invention can be aqueous compositions. In certain aspects, the ratio of any ingredient within the composition when compared to another ingredient (e.g., vitamin C to essential oil(s), vitamin C to silicone containing compound, silicone containing compound to essential oil, vitamin C to phytantriol, etc.) can be from about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 50:1, 60:1, 70:1, 80:1, 90:1, 100:1, or more or any number derivable therein, by weight or volume of the total composition. In other aspects, the ratio of any ingredient within the composition when compared to another ingredient (e.g., vitamin C to essential oil(s), vitamin C to silicone containing compound, silicone containing compound to essential oil, vitamin C to phytantriol, etc.) can be from about 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:50, 1:60, 1:70, 1:80, 1:90, 1:100, or more or any number derivable therein, by weight or volume of the total composition.

In other non-limiting embodiments, the compositions of the invention include less than about 50% by weight of the silicon containing compound (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49%). Other ranges for the amount of the silicone containing compound in the composition are contemplated and provided in other sections of this specification. In certain embodiments, the silicone containing compound is cyclomethicone. However, it should be recognized that other silicone containing compounds disclosed in other sections of this specification and those known to a person of ordinary skill in the art are contemplated as being useful with the present invention. In certain aspects, the ascorbic acid is suspended within the silicone containing compound or the essential oil, or both.

Non-limiting examples of essential oils that can be used within the context of the present invention include those identified in this specification and those known to a person of ordinary skill in the art. For example, the essential oil can be sesame oil, macadamia nut oil, tea tree oil, evening primrose oil, Spanish sage oil, Spanish rosemary oil, Coriander oil, Thyme oil, or Pimento berries oil. In other aspects, the essential oil can be a combination of at least 2, 3, 4, 5, 6, 7, 8, 9, 10, 11, 12, 13, 14, 15, 16, 17, 18, 19, 20, 21, 22, 23, 24, 25, 30, 40, or 50 or more different essential oils contemplated by the invention. In certain aspects, the compositions of the present invention can include a combination of all of the following essential oils: sesame oil; macadamia nut oil; tea tree oil; evening primrose oil; Spanish sage oil; Spanish rosemary oil; Coriander oil; Thyme oil; and Pimento berries oil. The compositions of the present invention, in certain embodiments, do not include a non-volatile oil.

In another non-limiting embodiment, the compositions of the present invention can include a thickening agent, including thickeners or gelling agents. In certain aspects, the thickening agent is trihydroxystearin or hydrogenated polyisobutene, or a combination of both. However, it should be recognized that other thickening agents disclosed in other sections of this specification and those known to a person of ordinary skill in the art are contemplated as being useful with the present invention. The compositions of the present invention, in certain non-limiting embodiments, include at least about 5% to about 15% or about 7% to about 10% by weight of the total composition of the thickening agent. However, as noted in other parts of this specification, the amount of the thickening agent in the compositions can extend beyond these stated ranges.

In other aspects of the present invention, the compositions are not emulsions. The compositions, in certain embodiments, do not include emulsifiers or a surfactants, or both. However, as explained in other sections of this specification, the compositions can be emulsions and can include emulsifiers or surfactants, or both. The compositions in non-limiting aspects can have a pH of about 6 to about 9. In other aspects, the pH can be 1, 2, 3, 4, 5, 6, 7, 8, 9, 10, 11, 12, 13, or 14.

The compositions of the present invention can also be storage stable (e.g., the ingredients can remain stable or active during and/or after storage). In certain aspects, the compositions are storage stable when stored for at least 1, 2, 3, 4, 5, or 6 days, 1, 2, 3, or 4 weeks, 1, 2, 3, 4, 5, 6, 7, 8, 9, 10, 11, or 12 months, or 1, 2, 3, 4, 5, 6, 7, 8, 9, or 10 or more years at room temperature. In other non-limiting embodiments, the ascorbic acid in the compositions can remain stable or active when the composition is stored for at least 1, 2, 3, 4, 5, or 6 days, 1, 2, 3, or 4 weeks, 1, 2, 3, 4, 5, 6, 7, 8, 9, 10, 11, or 12 months, or 1, 2, 3, 4, 5, 6, 7, 8, 9, or 10 or more years at room temperature. In yet another non-limiting aspect, at least 1, 5, 10, 15, 20, 30, 40, 50, 60, 70, 80, 90, 95, 96, 97, 98, 99, or 100% of the initial amount of the ascorbic acid remains stable or after the composition is stored for at least 1, 2, 3, 4, 5, or 6 days, 1, 2, 3, or 4 weeks, 1, 2, 3, 4, 5, 6, 7, 8, 9, 10, 11, or 12 months, or 1, 2, 3, 4, 5, 6, 7, 8, 9, or 10 or more years at room temperature.

The compositions of the present invention, in other non-limiting embodiments, can be formulated as cosmetic compositions. The compositions can be formulated for topical application to skin. The compositions can be included in a cosmetic vehicle. Non-limiting examples of cosmetic vehicles are disclosed in other sections of this specification and are known to those of skill in the art. Examples of cosmetic vehicles include emulsions (e.g., oil in water and water in oil emulsions), creams, lotions, solutions (e.g., aqueous or hydro-alcoholic solutions), anhydrous bases (e.g., lipstick or a powder), gels, and ointments. In other non-limiting embodiments, the compositions of the present invention can be included in anti-aging, cleansing, or moisturizing products. The compositions can also be formulated to include a non-aqueous nonpolar organic solvent. In certain aspects, the non-aqueous nonpolar organic solvent comprises cyclomethicone or trihydroxystearin, or a combination of both. The compositions can also be formulated for topical skin application at least 1, 2, 3, 4, 5, 6, 7, or more times a day during use. In other embodiments, the compositions of the present invention can be formulated as food compositions, pharmaceutical compositions, injectible compositions, etc.

In certain aspects, the compositions of the present invention include from about 7% to about 10% by weight of the s ascorbic acid or a derivative thereof, from about 20% to about 30% by weight of the silicone containing compound, and from about 40% to about 50% by weight of the essential oil or a mixture of essential oils. The composition can also include from about 7% to about 10% by weight of a thickener.

In other embodiments, the compositions can include vitamin E. The vitamin E can be tocopherol or tocopheryl acetate. The compositions can include vitamin A. The vitamin A can be vitamin A palmitate, retinyl palmitate, or retinoic acid. The compositions can include beta carotene, phytantriol (CAS No. 74563-64-7), or a triglyceride. Non-limiting tryglycerides include those identified in other sections of this specification and those known to a person of ordinary skill in the art. Examples of such tryglycerides include small, medium, and large chain triglycerides. In certain aspects, the triglyceride is a medium chain triglyceride (e.g., caprylic/capric triglyceride). The compositions can also include preservatives. Non-limiting examples of preservatives include methylparaben, propylparaben, or a mixture of methylparaben and propylparaben.

In still another aspect of the present invention, the inventor contemplates a method of treating or preventing a skin condition comprising topically applying the compositions of the present invention to the skin. Non-limiting examples of skin conditions include pruritus, spider veins, lentigo, age spots, senile purpura, keratosis, melasma, blotches, fine lines or wrinkles, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, etc. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein. The method can also include topically applying an amount effective to: increase the stratum corneum turnover rate of the skin; increase collagen synthesis in fibroblasts; increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids); inhibit melanin production in melanocytes; reduce or prevent oxidative damage to skin (including reducing the amount lipid peroxides and/or protein oxidation in the skin). In certain embodiments, the method includes applying the composition to the skin at least 1, 2, 3, 4, 5, 6, 7, or more times a day.

Another embodiment of the present invention concerns a method of preparing a storage stable vitamin C composition. The method can include obtaining ascorbic acid, or a derivative of ascorbic acid, obtaining a silicone containing compound, obtaining an essential oil, mixing the ascorbic acid, or a derivative of ascorbic acid, the silicone containing compound, and the essential oil to obtain a composition, wherein the ascorbic acid (or ascorbic acid derivative) in the composition is stable or active. In certain aspects, at least 1, 5, 10, 15, 20, 30, 40, 50, 60, 80, 90, 95, 96, 97, 98, 99, or 100% of the initial amount of the ascorbic acid (or its derivative) remains stable or active when the composition is stored for at least 1, 2, 3, 4, 5, or 6 days, 1, 2, 3, or 4 weeks, 1, 2, 3, 4, 5, 6, 7, 8, 9, 10, 11, or 12 months, or 1, 2, 3, 4, 5, 6, 7, 8, 9, or or more years at room temperature. In certain aspects, the ascorbic acid is particulate ascorbic acid. The ascorbic acid can be insoluble in the composition. The composition can be non-aqueous. The composition can include other characteristics or ingredients identified in this specification and those known to a person of ordinary skill in the art.

The inventor also contemplates a kit that includes the compositions of the present invention. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated by the inventor is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, or an anti-aging product.

It is contemplated that any embodiment discussed in this specification can be implemented with respect to any method or composition of the invention, and vice versa. Furthermore, compositions of the invention can be used to achieve methods of the invention.

A "non-volatile oil" includes those substance that will not evaporate at ordinary or room temperature.

The term "vitamin C" or "ascorbic acid" includes L-ascorbic acid, and derivatives thereof.

The terms "dissolved," "dissolving," or any variation of these terms means that the ascorbic acid is partially or completely solubilized in the compositions of the present invention.

The term "suspend," "suspended," or any variation of these terms causing the ascorbic acid to be partially or completely dispersed in the compositions of the present invention.

"Room temperature" includes the ambient temperature of a given room (e.g., a lab, medicine cabinet, bathroom, etc.), and in most normal cases, this would encompass a temperature of about 20° C. to about 25° C.

The terms "mixture," "mix," and "mixing" or any variants of these terms, when used in the claims and/or specification includes, stirring, blending, dispersing, milling, homogenizing, and other similar methods. The mixing of the components or ingredients of the disclosed compositions can form into a solution. In other embodiments, the mixtures may not form a solution. The ingredients/components can also exist as undissolved colloidal suspensions.

The term "about" or "approximately" are defined as being close to as understood by one of ordinary skill in the art, and in one non-limiting embodiment the terms are defined to be within 10%, within 5%, within 1%, or within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

In today's image conscious society, people are continually looking for a product that can improve the visual appearance of their skin. Vitamin C has been shown to exert a multitude of beneficial effects for human skin. For instance, because of its anti-oxidant properties, it has the ability to inhibit toxic free-radicals from damaging skin. This can be important for people who smoke or are often times around smokers or who are exposed to excessive amounts of sunlight or air-pollution—i.e., known causes of free-radical damage to skin.

Vitamin C is also an essential nutrient for the production of skin collagen (a protein that provides the skin with its elasticity). As people age, the collagen content of the skin declines. Additionally, sun exposure can accelerate the age-related collagen loss from skin. Vitamin C can help reduce or even reverse this age-related decline in the skin's collagen content.

Further, vitamin C has been shown to regenerate the skin's vitamin E content. Similar to vitamin C, vitamin E has antioxidant properties that are beneficial for protecting skin. Therefore, vitamin C has the ability to regenerate the skin's vitamin E content which provides an added level of protection from antioxidant damage to skin.

Also, as people age they suffer from restricted blood circulation to the skin. Because of this, the skin can be deprived of the vitamin C that is obtained from dietary or supplemental sources. Therefore, topical application of vitamin C becomes more important as a person ages.

The inventor has discovered a non-aqueous cosmetic composition that has the ability to stabilize vitamin C for extended periods of times. In certain non-limiting aspects, the composition can include: ascorbic acid or a derivative thereof; a silicone containing compound; and an essential oil or a mixture of essential oils. These and other aspects of the present invention are described in further detail in the following sections.

A. VITAMIN C AND DERIVATIVES OF VITAMIN C

Vitamin C is a water soluble vitamin that can be derived from glucose via the uronic acid pathway. As an antioxidant, vitamin C can neutralize free radicals which seek out electrons to regain their stability. Vitamin C is one source of electrons for free-radicals. Because of this, vitamin C can prevent free radicals from extracting electrons from sources where they could cause a great deal of damage to skin (e.g., skin cells, proteins, etc.).

The stable form of vitamin C is ascorbic acid. The chemical name for vitamin C is 2-oxo-L-threo-hexono-1,4-lactone-2,3-ene-diol (also known as Ascorbic Acid or L-ascorbic acid). CAS numbers associated with ascorbic acid include CAS Nos. 50-81-7 (L-Form) and 62624-30-0. The chemical structure for stable vitamin C is:

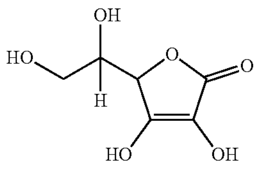

Ascorbic Acid

Derivatives of vitamin C are also contemplated as being useful in the context of the present invention. In certain aspects, "derivative" refers to a chemically modified compound that still retains the desired effects of the compound (e.g., vitamin C) prior to the chemical modification. Therefore, vitamin C derivatives can be equivalent to vitamin C in that the derivatives can retain similar effects of the vitamin C compound. Non-limiting examples of such derivatives include ascorbic acid polypeptide, ascorbyl dipalmitate, ascorbyl methylsilanol pectinate, ascorbyl palmitate, ascorbyl stearate, sodium ascorbyl palmitate, disodium ascorbyl sulfate, esters of ascorbic acid, magnesium ascorbate, magnesium ascorbyl phosphate, methylsilanol ascorbate, potassium ascorbyl tocopheryl phosphate, sodium ascorbate, ascorbyl glucoside, or ascorbyl tocopheryl maleate.

The inventor also contemplates that the following modifications to the vitamin C structure can be made in the context of the present invention. Non-limiting examples of such modifications include the addition or removal of lower alkanes such as methyl, ethyl, propyl, or substituted lower alkanes such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, hetero atoms such as N, S, or O can be substituted into the structure instead of a carbon atom.

B. SILICONE CONTAINING COMPOUNDS

Silicone containing compounds can have beneficial effects when used in the context of the present invention. These compounds, for example, have the ability to substantially prevent absorption of water or oxygen into compositions. Because of water or oxygen's ability to de-stabilize vitamin C, excluding these elements can be helpful in maintaining the stability of the vitamin C.

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Michigan. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Michigan.

C. ESSENTIAL OILS

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker.

Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant or vegetable from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention (e.g., International Cosmetic Ingredient Dictionary, 10th edition, 2004, which is incorporated by reference).

D. THICKENING AGENTS

Thickening agents, including thickener or gelling agents, include substances which that can increase the viscosity of a composition. Thickeners includes those that can increase the viscosity of a composition without substantially modifying the efficacy of the ingredients within the composition. Thickeners can also increase the stability of the compositions of the present invention. In certain aspects of the present invention, thickeners include hydrogenated polyisobutene or trihydroxystearin, or a mixture of both. Other examples include fumed silica and/or other silicone based thickeners.

Non-limiting examples of additional thickeners that are known to those of ordinary skill in the art can be used in the context of the present invention (e.g., U.S. Pat. Nos. 4,509,949; 2,798,053; International Cosmetic Ingredient Dictionary, 10th edition, 2004, all of which are incorporated by reference). Examples include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379.

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (e.g., hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

E. EQUIVALENTS

Known and unknown equivalents to the ingredients discussed throughout this specification can be used with the compositions and methods of the present invention. The equivalents can be used as substitutes for the ingredients. The equivalents can also be used to add to the methods and compositions of the present invention. A person of ordinary skill in the art would be able to recognize and identify acceptable known and unknown equivalents to the ingredients without undue experimentation.

F. COMPOSITIONS OF THE PRESENT INVENTION

A person of ordinary skill would recognize that the compositions of the present invention can include any number of combinations of the ingredients (e.g., vitamin C, derivatives of vitamin C, silicone containing compounds, essential oils, thickening agents, sun blocking agents, moisturizing agents, anti-oxidants, sunscreens having UVA and/or UVB protection, emollients, anti-irritants, vitamins, trace metals, anti-microbial agents, botanical extracts, fragrances, dyes and color ingredients, structuring agents, emulsifiers, etc.) discussed throughout this specification. It is also contemplated that that the concentrations of the ingredients can vary. In non-limiting embodiments, for example, the compositions may include in their final form, for example, at least about 0.0001%, 0.0002%, 0.0003%, 0.0004%, 0.0005%, 0.0006%, 0.0007%, 0.0009%, 0.0010%, 0.0011%, 0.0012%, 0.0013%, 0.0014%, 0.0015%, 0.0016%, 0.0018%, 0.0019%, 0.0020%, 0.0021%, 0.0022%, 0.0023%, 0.0024%, 0.0025%, 0.0027%, 0.0028%, 0.0029%, 0.0030%, 0.0031%, 0.0032%, 0.0033%, 0.0034%, 0.0036%, 0.0037%, 0.0038%, 0.0039%, 0.0040%, 0.0041%, 0.0042%, 0.0043%, 0.0045%, 0.0046%, 0.0047%, 0.0048%, 0.0049%, 0.0050%, 0.0051%, 0.0052%, 0.0054%, 0.0055%, 0.0056%, 0.0057%, 0.0058%, 0.0059%, 0.0060%, 0.0061%, 0.0063%, 0.0064%, 0.0065%, 0.0066%, 0.0067%, 0.0068%, 0.0069%, 0.0070%, 0.0072%, 0.0073%, 0.0074%, 0.0075%, 0.0076%, 0.0077%, 0.0078%, 0.0079%, 0.0081%, 0.0082%, 0.0083%, 0.0084%, 0.0085%, 0.0086%, 0.0087%, 0.0088%, 0.0090%, 0.0091%, 0.0092%, 0.0093%, 0.0094%, 0.0095%, 0.0096%, 0.0097%, 0.0099%, 0.0100%, 0.0200%, 0.0250%, 0.0275%, 0.0300%, 0.0325%, 0.0350%, 0.0400%, 0.0425%, 0.0450%, 0.0475%, 0.0500%, 0.0525%, 0.0550%, 0.0575%, 0.0625%, 0.0650%, 0.0675%, 0.0700%, 0.0725%, 0.0750%, 0.0775%, 0.0800%, 0.0850%, 0.0875%, 0.0900%, 0.0925%, 0.0950%, 0.0975%, 0.1000%, 0.1250%, 0.1750%, 0.2000%, 0.2250%, 0.2500%, 0.2750%, 0.3000%, 0.3250%, 0.3500%, 0.4000%, 0.4250%, 0.4500%, 0.4750%, 0.5000%, 0.5250%, 0.0550%, 0.5750%, 0.6250%, 0.6500%, 0.6750%, 0.7000%, 0.7250%, 0.7500%, 0.7750%, 0.8000%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or more, or any range or integer derivable therein, of at least one of the ingredients mentioned throughout the specification and claims. In non-limiting aspects, the percentage can be calculated by weight or volume of the total composition. A person of ordinary skill in the art would understand that the concentrations can vary depending on the desired effect of the composition and/or on the product into which the composition is incorporated into.

G. VEHICLES

The compositions of the present invention can be incorporated into all types of vehicles. Non-limiting examples of suitable vehicles include emulsions (e.g., water-in-oil, water-in-oil-in-water, oil-in-water, oil-in-water-in-oil, oil-in-water-in-silicone emulsions), creams, lotions, solutions (both aqueous and hydro-alcoholic), anhydrous bases (such as lipsticks and powders), gels, and ointments or by other method or any combination of the forgoing as would be known to one of ordinary skill in the art (Remington's, 1990). Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

H. COSMETIC PRODUCTS

The composition of the present invention can also be used in many cosmetic products including, but not limited to, sunscreen products, sunless skin tanning products, hair products, finger nail products, moisturizing creams, skin benefit creams and lotions, softeners, day lotions, gels, ointments, foundations, night creams, lipsticks, cleansers, toners, masks, or other known cosmetic products or applications. Additionally, the cosmetic products can be formulated as leave-on or rinse-off products. In certain aspects, the compositions of the present invention are stand-alone products.

I. ADDITIONAL COMPOUNDS, AGENTS, AND INGREDIENTS THAT CAN BE USED IN COMBINATION WITH THE PRESENT COMPOSITIONS

Compositions of the present invention can include other beneficial agents and compounds such as, for example, sun blocking agents, acute or chronic moisturizing agents (including, e.g., humectants, occlusive agents, and agents that affect the natural moisturization mechanisms of the skin), anti-oxidants, sunscreens having UVA and/or UVB protection, emollients, anti-irritants, vitamins, trace metals, anti-microbial agents, botanical extracts, fragrances, dyes and color ingredients, structuring agents, and/or emulsifiers (see U.S. Pat. No. 6,290,938).

1. Sunblock Agents

Sunblock agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (and octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxy-cinnamate and ethyl methoxycinnamate), cinnamate esters, salicylates (homomethyl salicylate, benzyl salicylate, glycol salicylate, isopropylbenzyl salicylate), anthranilates, ethyl urocanate, homosalate, and Parsol 1789. Non-limiting examples of physical sunblocks include kaolin, talc and metal oxides (e.g., titanium dioxide and zinc oxide). Non-limiting examples of additional sun block agents that are known to those of ordinary skill in the art can be used in the context of the present invention (e.g., International Cosmetic Ingredient Dictionary, 10th edition, 2004, which is incorporated by reference).

2. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, acrylates/C10-30 alkyl acrylate crosspolymer, acrylates copolymer, alanine, algae extract, aloe barbadensis, aloe-barbadensis extract, aloe barbadensis gel, althea officinalis extract, aluminum starch octenylsuccinate, aluminum stearate, apricot (prunus armeniaca) kernel oil, arginine, arginine aspartate, arnica montana extract, ascorbic acid, ascorbyl palmitate, aspartic acid, avocado (persea gratissima) oil, barium sulfate, barrier sphingolipids, butyl alcohol, beeswax, behenyl alcohol, beta-sitosterol, BHT, birch (betula alba) bark extract, borage (*Borago officinalis*) extract, 2-bromo-2-nitropropane-1,3-diol, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamon (*Elettaria cardamomum*) oil, carnauba (*Copernicia cerifera*) wax, carrageenan (*Chondrus crispus*), carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*)oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, eucalyptus globulus oil, evening primrose (*Oenothera biennis*) oil, fatty acids, tructose, gelatin, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, honey, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (citrus medica limonum) oil, linoleic acid, linolenic acid, macadamia ternifolia nut oil, magnesium stearate, magnesium sulfate, maltitol, matricaria (chamomilla recutita) oil, methyl glucose sesquistearate, methylsilanol PCA, microcrystalline wax, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, salicylic acid, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil. Non-limiting examples of additional moisturizing agents that are known to those of ordinary skill in the art can be used in the context of the present invention (e.g., International Cosmetic Ingredient Dictionary, 10th edition, 2004, which is incorporated by reference).

3. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCI, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite. Non-limiting examples of additional antioxidants that are known to those of ordinary skill in the art can be used in the context of the present invention (e.g., International Cosmetic Ingredient Dictionary, 10th edition, 2004, which is incorporated by reference).

4. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

5. Emulsifiers

In certain aspects of the present invention, the compositions do not include an emulsifier. In other aspects, however, the compositions can include one or more emulsifiers. Emulsifiers can reduce the in interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof. Non-limiting examples of additional emulsifiers that are known to those of ordinary skill in the art can be used in the context of the present invention (e.g., International Cosmetic Ingredient Dictionary, 10th edition, 2004, which is incorporated by reference).

6. Additional Compounds and Agents

Non-limiting examples of additional compounds and agents that can be used with the compositions of the present invention include, vitamins (e.g. D, E, A, and K), trace metals (e.g. zinc, calcium and selenium), anti-irritants (e.g. steroids and non-steroidal anti-inflammatories), botanical extracts (e.g. aloe vera, chamomile, cucumber extract, *Ginkgo biloba*, ginseng, and rosemary), dyes and color ingredients (e.g. D&C blue no. 4, D&C green no. 5, D&C orange no. 4, D&C red no. 17, D&C red no. 33, D&C violet no. 2, D&C yellow no. 10, D&C yellow no. 11 and DEA-cetyl phosphate), emollients (i.e. organic esters, fatty acids, lanolin and its derivatives, plant and animal oils and fats, and di- and triglycerides), antimicrobial agents (e.g., triclosan and ethanol), and fragrances (natural and artificial).

J. KITS

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions (e.g., foundations), or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other dispersions or compositions included in the container. Instructions can include an explanation of how to apply, use, and maintain the products, dispersions, or compositions.

K. EXAMPLES

The following examples are included to demonstrate certain non-limiting aspects of the invention. It should be appreciated by those of skill in the art that the techniques disclosed in the examples which follow representative techniques discovered by the inventor to function well in the practice of the invention. However, those of skill in the art should appreciate that changes can be made in the specific embodiments which are disclosed and still obtain a like or similar result without departing from the spirit and scope of the invention.

1. Example 1

A non-limiting example of one embodiment of the present invention is exhibited in Table 1. The ingredients in Table 1 provide a stabilized vitamin C composition.

TABLE 1

| | Ingredient | % Concentration (by weight) |
|---|---|---|
| 1. | Vitamin C* | 9.13 |
| 2. | Sesame oil | 46.739** |
| 3. | Cyclomethicone | 26.99 |
| 4. | Trihydroxystearin | 5.73 |
| 5. | Hydrogenated polyisobutene | 5.454 |
| 6. | Caprylic/capric triglyceride | 3.6 |
| 7. | Macadamia nut oil | 0.5454 |
| 8. | Phytantriol | 0.054 |
| 9. | Tea tree oil | 0.054 |
| 10. | Tocopherol | 0.2727 |
| 11. | Evening primrose oil | 0.054 |
| 12. | Spanish sage oil | 0.054 |
| 13. | Spanish rosemary oil | 0.054 |
| 14. | Coriander oil | 0.054 |
| 15. | Thyme oil | 0.054 |
| 16. | Pimento berries oil | 0.054 |
| 17. | Vitamin A palmitate | 0.54 |
| 18. | Methylparaben | 0.54 |
| 19. | Propylparaben | 0.027 |
| 20. | Beta carotene | 0.00054 |
| | TOTAL | 100 |

*The vitamin C in this non-limiting embodiment is Ultra Fine Vitamin C powder. Add ingredients 2-20 one at a time in sequential order into a kitchenette planetary mixing equipment. Continuously mix while each ingredient is added. Subsequently, add vitamin C in small intervals and continue mixing. All mixing procedures are performed at room temperature.

**Sesame oil was rounded up to 46.739.

2. Example 2—Vitamin C Stability Study

The composition described in Table 1 was stored at room temperature (approximately 70-75° F.) for approximately ten years. Subsequently, the composition was tested to determine the amount of stable vitamin C remaining in the composition. The testing procedure included dispersing the composition in methyl alcohol. Vitamin C was subsequently extracted from the sample with purified water. The stability of the vitamin C was calculated by an external standard method using reverse phase HPLC using a variable wavelength detector (a detailed description of the testing method used is provided in Example 3). The results are shown in Table 2.

TABLE 2

| Year | % of Stable Vitamin C in the Composition |
|---|---|
| 0 | 9.13 |
| 10 | 8.91 |

After approximately ten years of room temperature storage, 97.6% of stable vitamin C remained in the composition. Additionally, there was no significant discoloration in the aged composition.

3. Example 3—Testing Vitamin C Stability

A non-limiting method that was used to test vitamin C stability in the composition in Table 1 is described in the following paragraphs.

Apparatuses Used: HPLC with variable wavelength UV detector and integrator (recommended settings include UV@255 nm, flow rate at 0.75 mL/min, sample size 5 μL, temperature at 35° C.); $NH_2$ column, 5μ, 25 cm×4.6 mm (Whatman, Inc. catalogue #4691-3371); Analytical balance (read to 0.1 mg); Volumatric flasks (100 mL); Filtering discs (nylon 0.45μ) Vortex; Sonicator.

Reagents Used: Ascorbyl palmitate; Ascrobic acid; Methanol; Potassium Phosphate (monobasic); Phosphoric acid.

Calibration Standard Used: Weigh about 20 mg (0.02 g) each of ascorbyl palmitate and ascorbic acid into a 100 mL volumetric flask. Add a sufficient amount of methanol to disperse the reagents and sonicate for about ten minutes. Fill up to 100 mL mark with methanol and mix. Prepare the calibration standard fresh.

Mobile Phase Used: 70:30 Methanol/0.02 M Potassium Phosphate Solution. Dissolve 2.70 g of potassium phosphate monobasic in 1 liter of purified water and adjust the pH to 3.5 with phosphoric acid. Filter and mix 30 parts of this solution with 70 parts methanol.

Sample Preparation Used: Calculate the appropriate sample weight from the following equation:

$$\frac{0.025 \times 100}{\text{Expected \% of Ascorbyl Palmitate or Ascorbic Acid}}$$

Weigh the sample into a 100 mL volumetric flask and record the accurate weight to 0.1 mg. Add a sufficient amount of methanol to disperse the sample and sonicate for about 2 to 10 minutes. Fill up to 100 mL mark with methanol and mix. Filter the solution using a 0.45μ filtering disc into a sample vial. Prepare samples in duplicate.

Calibration of HPLC: Calibrate the instrument with the standard solution. Make at least three injections and obtain response factors. The relative standard deviation of the response factors should not exceed 3.0%. The tailing factor should be less than 1.5.

Testing Procedure Used: Inject sample solution in duplicate and calculate the average of the results. Compare the absolute retention time of the analyte peak in the calibration run to the respective peak in the sample run. If the retention times differ by more than 5% relative, repeat the calibration and sample runs. Calculate the relative retention time (RRT) between calibration and sample runs as follows:

$$RRT = \frac{RTs - RTc \times 100}{RTc}$$

where,

RTs=Retention Time of I.Std or analyte peak in sample run

RTc=Retention Time of I.Std or analyte peak in calibration run

100=100 Percent

Wash the system with 30:70 methanol:water for about 30 minutes after the analysis is completed.

All of the compositions and/or methods disclosed and claimed in this specification can be made and executed without undue experimentation in light of the present disclosure. While the compositions and methods of this invention have been described in terms of certain embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. U.S. Pat. No. 2,400,171
2. U.S. Pat. No. 2,798,053
3. U.S. Pat. No. 3,755,560
4. U.S. Pat. No. 4,421,769
5. U.S. Pat. No. 4,599,379
6. U.S. Pat. No. 4,628,079
7. U.S. Pat. No. 4,835,206
8. U.S. Pat. No. 4,849,484
9. U.S. Pat. No. 4,509,949
10. U.S. Pat. No. 5,100,660
11. U.S. Pat. No. 5,011,681
12. U.S. Pat. No. 5,087,445
13. U.S. Pat. No. 6,146,664
14. U.S. Pat. No. 6,290,938
15. Fitzpatrick et al., *Dermatol. Surg.*, 28(3):231-236, 2002.
16. Humbert, *Eur. J. Dermatol.*, 11(2):172-173, 2001.

17. International Cosmetic Ingredient Dictionary, 10th edition, 2004
18. Lin et al., *J. Am. Acad. Dermatol.,* 48(6):866-874, 2003.
19. McCutcheon's, Detergents and Emulsifiers, North American Edition (1986).
20. Pinnell, *J. Am. Acad. Dermatol.,* 48(1):1-19; quiz 20-22, 2003.
21. Remington's Pharmaceutical Sciences, 18th Ed. Mack Printing Company, 1289-1329, 1990.
22. Schiltz et al. *J. Investigative Dermatology,* 87:663-667, 1986.

The invention claimed is:

1. A composition comprising:
(a) ascorbic acid;
(b) a silicone oil; and
(c) at least 15% by weight of an essential oil;
wherein at least 50% of the initial amount of ascorbic acid in the composition remains stable when the composition is stored for at least 1 month at room temperature.

2. The composition of claim 1, wherein the composition comprises at least 10% by weight of the ascorbic acid.

3. The composition of claim 2, wherein the silicone oil comprises dimethicone or polysilicone-11.

4. The composition of claim 1, wherein the composition further comprises hyaluronic acid.

5. The composition of claim 1, wherein the essential oil comprises orange oil and lemon oil.

6. The composition of claim 1, wherein the ascorbic acid comprises L-ascorbic acid or ascorbyl glucoside.

7. The composition of claim 1, wherein the ascorbic acid comprises an ester of ascorbic acid.

8. The composition of claim 1, wherein the composition is not an emulsion.

9. The composition of claim 1, wherein the composition does not include an emulsifier or a surfactant.

10. The composition of claim 1, wherein at least 75% of the initial amount of the ascorbic acid in the composition remains stable when the composition is stored for at least 1 month at room temperature.

11. The composition of claim 10, wherein at least 90% of the initial amount of the ascorbic acid in the composition remains stable when the composition is stored for at least 1 month at room temperature.

12. The composition of claim 1, wherein the composition comprises 25 wt. % to 50 wt. % of the essential oil.

13. The composition of claim 1, wherein the composition comprises at least 25 wt. % of the essential oil.

14. The composition of claim 1, wherein the composition comprises less than 50 wt. % of the silicone containing compound.

15. The composition of claim 1, wherein the vitamin C is suspended in the composition.

16. The composition of claim 1, wherein the vitamin C is solubilized in the composition.

17. The composition of claim 1, wherein the composition is a topical skin formulation.

18. The composition of claim 1, wherein the composition is a pharmaceutical composition.

19. A method of treating a skin condition, the method comprising topically applying the composition of claim 1 to skin in need thereof, wherein topical application treats the skin condition.

20. The method of claim 19, wherein the skin condition is a fine line or wrinkle, and wherein the composition is applied to the fine line or wrinkle.

* * * * *